US009750555B2

(12) United States Patent
Wittenberger et al.

(10) Patent No.: US 9,750,555 B2
(45) Date of Patent: Sep. 5, 2017

(54) METHOD AND APPARATUS FOR CRYOADHESION

(71) Applicant: Medtronic CryoCath LP, Toronto (CA)

(72) Inventors: Dan Wittenberger, L'Ile-Bizard (CA); Rachid Mahrouche, Lasalle (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 123 days.

(21) Appl. No.: 14/696,873

(22) Filed: Apr. 27, 2015

(65) Prior Publication Data

US 2015/0223860 A1 Aug. 13, 2015

Related U.S. Application Data

(62) Division of application No. 13/803,075, filed on Mar. 14, 2013, now abandoned.

(51) Int. Cl.

*A61B 18/02* (2006.01)
*A61B 18/14* (2006.01)
*A61B 18/00* (2006.01)
*A61F 7/00* (2006.01)

(52) U.S. Cl.

CPC .......... *A61B 18/02* (2013.01); *A61B 18/1492* (2013.01); *A61B 2018/0022* (2013.01); *A61B 2018/00041* (2013.01); *A61B 2018/00351* (2013.01); *A61B 2018/00577* (2013.01); *A61B 2018/00994* (2013.01); *A61B 2018/0212* (2013.01); *A61B 2018/0262* (2013.01); *A61F 2007/0054* (2013.01)

(58) Field of Classification Search

CPC ........................................................ A61B 18/02

See application file for complete search history.

(56) References Cited

U.S. PATENT DOCUMENTS

| | | | |
|---|---|---|---|
| 5,452,582 | A | 9/1995 | Longsworth |
| 5,522,870 | A | 6/1996 | Ben-Zion |
| 2007/0032783 | A1 | 2/2007 | Abboud et al. |
| 2011/0092967 | A1 | 4/2011 | Harvey-Poncelet et al. |
| 2011/0152849 | A1 | 6/2011 | Baust et al. |

OTHER PUBLICATIONS

International Search Report and Written Opinion dated Jun. 11, 2014 for International Application Serial No. PCT/CA2014/000186, International Filing Date: Mar. 7, 2014 consisting of 8 pages.

International Search Report and Written Opinion dated May 30, 2014 for International Application Serial No. PCT/CA2014/000187, International Filing Date: Mar. 7, 2014 consisting of 8 pages.

*Primary Examiner* — Michael Kahelin

(74) *Attorney, Agent, or Firm* — Christopher & Weisberg, P.A.

(57) ABSTRACT

A method and system for continuously delivering cryotreatment to a treatment device. In one embodiment, the system may include a first PID circuit in the fluid delivery line and a second PID circuit in the fluid return line, and the first and second PID circuits may operate simultaneously to continuously provide coolant to a cryotreatment device during the inflation phase, ablation phase, and warming (or thawing) phase while providing for temperature adjustment. Alternatively, the system may include a bypass line by which coolant may bypass the subcooler system and be delivered to the cryotreatment device at non-ablation temperatures during the inflation phase. During the ablation phase, coolant may flow through the subcooler system.

12 Claims, 4 Drawing Sheets

METHOD AND APPARATUS FOR CRYOADHESION

CROSS-REFERENCE TO RELATED APPLICATION

This application is a divisional of patent application Ser. No. 13/803,075, filed Mar. 14, 2013, entitled METHOD AND APPARATUS FOR CRYOADHESION, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for delivering coolant to a cryotreatment device. Specifically, the present invention relates to a method and system for continuously delivering coolant to a cryotreatment device during an inflation phase, an ablation phase, and a warming phase.

BACKGROUND OF THE INVENTION

Cryotreatment, a therapy that uses that removal of heat from tissue, is often used to treat cardiac conditions such as cardiac arrhythmias. In most cryotreatment procedures, a pressurized refrigerant is circulated within the tip of a cryotreatment catheter, where the refrigerant expands and absorbs heat from surrounding tissue. As the tissue freezes, blood adjacent the treatment site may also freeze, creating an "ice ball" that temporarily adheres the treatment element (for example, a cryoballoon or thermally conductive area at the tip of the cryotreatment device) to the tissue at the treatment site, a phenomenon called cryoadhesion.

Cryoadhesion is advantageous in that it helps prevent the cryotreatment device from moving away from the target treatment site of a beating heart. However, research has shown that a freeze-thaw-freeze cycle more effectively ablates tissue than a single longer freeze-only cycle. Although more efficient lesion creation is desired, the freeze-thaw-freeze cycle may also result in the thawing of the ice ball that keeps the cryotreatment device in place. As a result, the device must be repositioned, which may be complicated and time-consuming. Further, some cryotreatment procedures, such pulmonary vein isolation (PVI), involve the use of fluoroscopy to visualize the position of the device and to make sure that, for example, the pulmonary vein is completely occluded. Fluoroscopy involves x-ray visualization; consequently, each time the ice ball thaws and the cryotreatment device is repositioned, the patient and the user are exposed to an increased amount of radiation.

In most cryotreatment systems that include an inflatable treatment element such as a cryoballoon, the system includes an inflation reservoir that is used to inflate the cryoballoon. An ablation procedure using systems such as this may require several stages. In the inflation stage, the inflation reservoir is filled with coolant at or near room temperature (that is, at temperatures not low enough to cause tissue ablation), and this volume is then used to inflate the cryoballoon, allowing for device positioning before the cryoballoon reaches ablation temperatures. The system may then enter one or more transition, ablation, evacuation, and refilling stages. Coolant flow may be stopped during the evacuation and refilling stages, and therefore the ice ball may be allowed to thaw and cryoadhesion may be broken.

Such fixed initial volume systems may only be used for a specific device, as the size of the inflation reservoir is predetermined, and cannot be adapted for use with, for example, a different type or size of device or newer generation of a device. If a user wants to substitute a different device, or even if a newer generation of a current device is developed, the entire system may have to be replaced. Additionally, these systems are generally "on/off" and do not easily allow for temperature modification during an ablation procedure.

Therefore, it is desirable to provide a method and system for more efficient cryotreatment, while reducing the need for fluoroscopy. It is also desirable to provide a continuous system that is usable with a variety of devices.

SUMMARY OF THE INVENTION

The present invention advantageously provides a method and system for delivering cryotreatment to a treatment device. In one embodiment, the system may include a fluid supply; a fluid injection line in communication with the fluid supply, the fluid injection line including a first PID circuit having a first PID controller, a first pressure transducer, and a first proportional valve; a cryotreatment device having a treatment element in communication with the fluid injection line; a fluid return line in communication with the cryotreatment device, the fluid return line including a second PID circuit having a second PID controller, a second pressure transducer, and a second proportional valve; and a vacuum source in communication with the fluid return line, the system being programmable to operate in an inflation phase, a treatment phase, and a warming phase, the first PID circuit and second PID circuit simultaneously operating to control the temperature of the treatment element during the inflation phase, the ablation phase, and the warming phase. The treatment element may define an expansion chamber, the expansion chamber being in communication with the fluid injection line and the fluid return line, the treatment element having an adjustable temperature based at least in part on the flow of fluid within the expansion chamber from the fluid supply reservoir. The system may further include a control unit in communication with the first PID circuit and the second PID circuit, first pressure transducer and the second pressure transducer each measuring pressure within the system, the control unit adjusting the first proportional valve and the second proportional valve based at least in part on the pressure measurements of the first proportional valve and the second proportional valve. For example, the temperature of the treatment element may be decreased when the first proportional valve is adjusted to increase the flow rate of coolant into the expansion chamber and when the second proportional valve is adjusted to at least partially open the expansion chamber to the vacuum source. Likewise, the temperature of the treatment element may be increased when the first proportional valve is adjusted to reduce the flow rate of coolant into the expansion chamber and when the second proportional valve is adjusted to at least partially close the expansion chamber to the vacuum source. The treatment element may be an inflatable element, which, once inflated, may remain inflated throughout the treatment phase and warming phase.

In another embodiment, the system may include a coolant supply; a fluid injection line in communication with the fluid supply, the fluid injection line including a subcooler; a bypass line in communication with the fluid injection line, the bypass line including a valve, an inlet upstream of the subcooler, and an outlet downstream of the subcooler; a cryotreatment device having a treatment element in communication with the fluid injection line; a fluid return line in communication with the cryotreatment device; and a vacuum source in communication with the fluid return line, the system being programmable to operate in an inflation phase, a treatment phase, and a warming phase, the coolant continuously flowing through the bypass line during the inflation phase and through the subcooler during the ablation phase. The treatment element may define an expansion chamber, the expansion chamber being in communication with the fluid injection line and the fluid return line, the treatment element having an adjustable temperature based at least in part on the flow of coolant within the expansion chamber. The bypass valve may be substantially open during the inflation phase and substantially closed during the ablation phase. Further, the bypass line may be substantially open during the warming phase.

In one embodiment, the method may include positioning a cryotreatment device including a treatment element defining an expansion chamber proximate the area of target tissue, the expansion chamber being in fluid communication with a fluid flow path, and continuously delivering coolant to the expansion chamber during the inflation phase, the ablation phase, and the warming phase, the first PID circuit operating to deliver coolant to the expansion chamber at a first flow rate during the inflation phase, a second flow rate during the ablation phase, and a third flow rate during the warming phase. The fluid flow path may include a fluid supply containing coolant, a fluid injection line in communication with the fluid supply and the expansion chamber, the fluid injection line including a first PID circuit having a first PID controller, a first pressure transducer, and a first proportional valve; a fluid return line in communication with the cryotreatment device, the fluid return line including a second PID circuit having a second PID controller, a second pressure transducer, and a second proportional valve; and a vacuum source in communication with the fluid return line, the system being programmable to operate in an inflation phase, an ablation phase, and a warming phase, the first PID circuit and second PID circuit simultaneously operating to control the flow rate of coolant into and out of the expansion chamber during the inflation phase, the ablation phase, and the warming phase.

In another embodiment, the method may generally include positioning a cryotreatment device including a treatment element defining an expansion chamber proximate the area of target tissue, the expansion chamber being in fluid communication with a fluid flow path, and continuously delivering coolant to the expansion chamber during the inflation phase, the ablation phase, and the warming phase, the bypass line valve being substantially open during the inflation phase and substantially closed during the ablation phase. The fluid flow path may include a coolant supply; a fluid injection line in communication with the fluid supply and the expansion chamber, the fluid injection line including a subcooler; a bypass line in communication with the fluid injection line, the bypass line including a valve, an inlet upstream of the subcooler, and an outlet downstream of the subcooler; a fluid return line in communication with the cryotreatment device; and a vacuum source in communication with the fluid return line, the system being programmable to operate in an inflation phase, an ablation phase, and a warming phase, the coolant flowing through the bypass line during the inflation phase and through the subcooler during the ablation phase.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
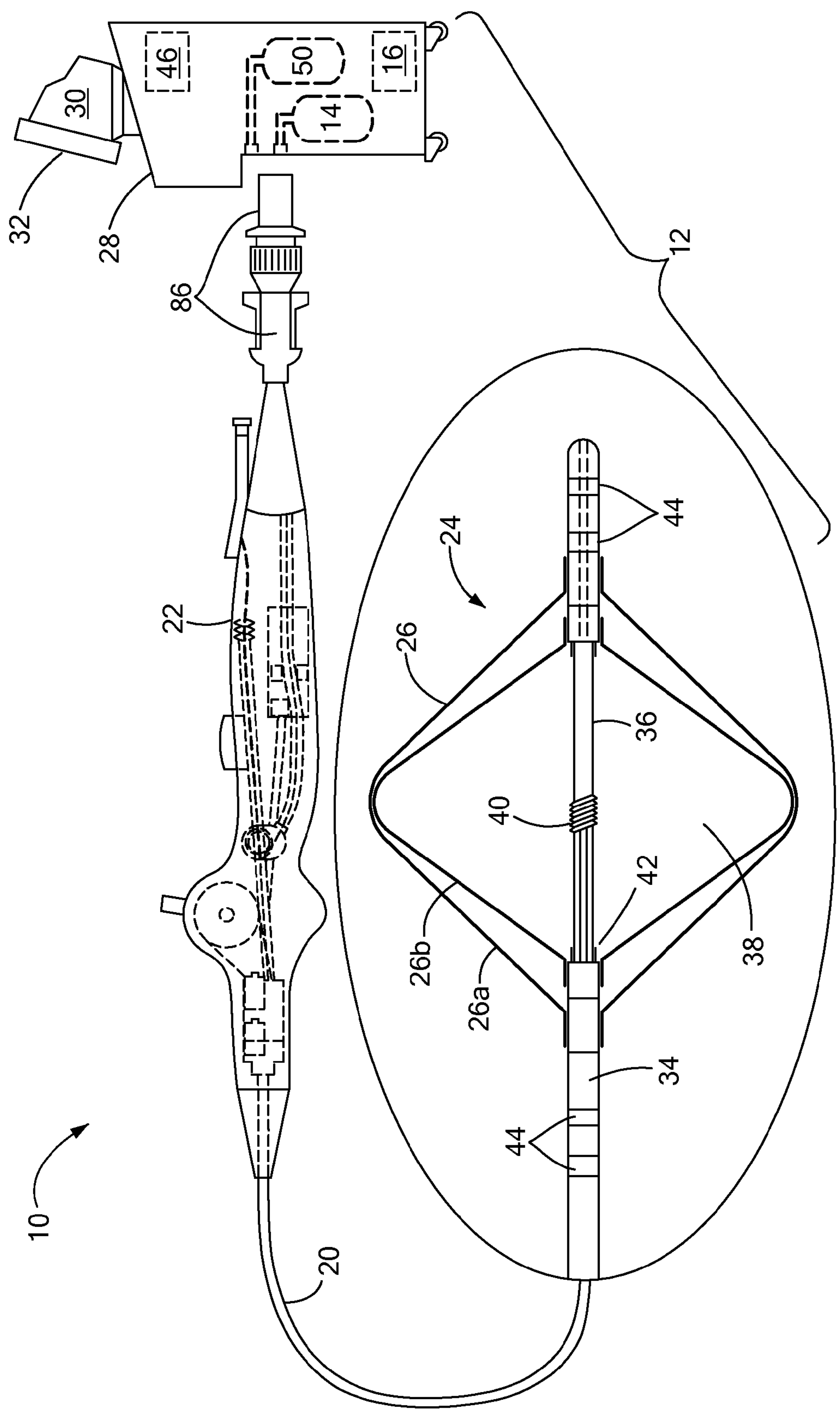
FIG. 1 shows a schematic view of a first embodiment of a continuous flow cryotreatment system in accordance with the present invention.

As described above, many currently known ablation systems are fixed initial volume systems. In these systems, a predetermined volume of fluid (e.g., coolant) that is specific to the device being used may be delivered to a fixed initial volume (inflation) reservoir from a fluid supply reservoir at room temperature or without being cooled. That is, the temperature is above cryotreatment or even cryocooling temperatures. For example, the initial volume of coolant may have a temperature that is close to, or slightly above, room temperature. During this step, the inflation reservoir is closed from a vacuum source. Once the initial volume is received within the inflation reservoir, a valve may be used to close the inflation reservoir from the fluid supply reservoir, thereby isolating the inflation reservoir. This initial volume of inflation fluid is a fixed volume and is specific to the cryotreatment system and the device being used. Therefore, if a user changes devices (for example, uses a device with a different balloon size or configuration), the new device cannot be used with an existing system, unless the appropriate fixed initial volume would be the same between the old and new device.

Once the inflation reservoir is filled, another valve may be used to open the inflation reservoir to the device, wherein the fixed initial volume inflates the cryoballoon to a predetermined inflation level. During the inflation phase, the cryoballoon may be closed to the vacuum pump or exhaust system so that the coolant does not exit the cryoballoon. After the inflation phase is over, the system enters into a transition phase, wherein a valve may be used to open, at least partially, the cryoballoon to the vacuum source. The ablation phase then begins that includes a continuous flow of coolant at ablation temperatures. That is, one or more valves may be opened or adjusted to allow coolant to both enter and exit the cryoballoon. If a thawing phase is desired, the injection of coolant from the fluid supply reservoir is stopped altogether. The system is then evacuated or flushed by using one or more valves to open the fluid flow path of the system to the vacuum or exhaust system. After evacuation and if another ablation phase is desired, the inflation reservoir is refilled with coolant. During the refilling phase, the fluid flow path of the system is open to the vacuum, except for the inflation reservoir.

In the fixed initial volume system, one or more valves in the injection line leading to the cryotreatment device and one or ore valves in the return line leading from the cryotreatment device are operated independently during the inflation, transition, and thawing phases. That is, during the inflation phase, the cryotreatment device is closed to the vacuum source and the fluid supply reservoir, but open to the inflation volume reservoir. During the transition phase, the cryotreatment device is at least partially opened to the vacuum source and fluid supply reservoir, but closed to the inflation volume reservoir. During the thawing phase, the cryotreatment device is fully closed to both inflation reservoir and fluid supply reservoir, but fully open to the vacuum source. The ablation phase is the only phase in which the cryotreatment device is open to both the fluid supply reservoir and the vacuum source.

As used herein, the terms "cryotreatment" or "treatment" refer to the thermal treatment of tissue. In particular, this thermal treatment involves the cooling of tissue to ablation or subablation temperatures. Although the continuous flow systems described herein may be well suited for cryoablation procedures in which tissue is permanently disrupted or destroyed. However, it will be understood that the continuous flow systems described herein may also be suited for other cryotreatment procedures in which tissue may be temporarily disrupted or destroyed, or procedures in which tissue is cooled to temperatures above those at which tissue is temporarily disrupted or destroyed.

Referring now to FIG. 1, an exemplary cryotreatment device 10 is shown that may be suitable for use in the continuous flow systems 12 described herein. In a continuous flow system 12, a cryotreatment device 10 may be open to both a fluid supply reservoir 14 and a vacuum source 16 during every phase of the procedure. Further, the continuous flow system 12 does not require a transition phase to move between the inflation phase and ablation phase. The cryotreatment device 10 is in communication with the fluid flow path 18 of the continuous flow cryotreatment system 12, and may generally define a proximal end 20 that may by coupled to a handle 22 and a distal end 24 that may include an inflatable cryotreatment element 26. The device 10 may be in communication with a control unit 28 that includes one or more controllers, processors, and/or software modules containing instructions or algorithms (collectively referred to as "computers 30") to provide for the automated operation and performance of the features, sequences, calculations, or procedures described herein. Further, the control unit 28 may include one or more displays or screens 32, user input devices, and other components required for adjusting, monitoring, and controlling the system 12.

As shown in the non-limiting example of FIG. 1, the inflatable cryotreatment element 26 may include an outer cryoballoon 26*a* and an inner cryoballoon 26*b*, at least a portion of each being coupled to the elongate body 34 of the device 10 and at least a portion of each being coupled to a shaft 36 that may be slidably and rotatably disposed within the elongate body 34 of the device 10. The inflatable cryotreatment element 26 may define an expansion chamber 38 in which the coolant may expand to cool the treatment element 26. Coolant may be delivered to the expansion chamber 38 through an injection lumen 40 (which may include one or more holes or openings and may be coupled to at least a portion of the shaft 36, as shown in FIG. 1) and expanded coolant may be recovered from the expansion chamber 38 through an exhaust lumen 42 in communication with a vacuum 16. The elongate body 34 and/or the shaft 36 may include one or more electrodes 44, such as mapping electrodes for recording electrocardiogram or monophasic action potential (MAP) signals or treatment electrodes in communication with an energy source 46 (such as radiofrequency, ultrasound, microwave, or other energy). Although cryotreatment devices 10 having inflatable treatment elements 26 are shown and described herein, the continuous flow cryotreatment systems 12 shown and described herein may also be used with cryotreatment devices having a fixed diameter, such as focal cryotreatment catheters. Further, a cryotreatment device 10 may be used that has one or more inflatable elements 26 in any of a myriad of sizes, shapes, and configurations. The system 12 may be configured to identify the cryotreatment device 10 being used by a smartchip or other identifying electronic component, and to adjust system 12 parameters as needed for the safe operation of the device 10. Alternatively, a user may manually input the identity of the device 10 and the system 12 may adjust as appropriate.

Figure 2:
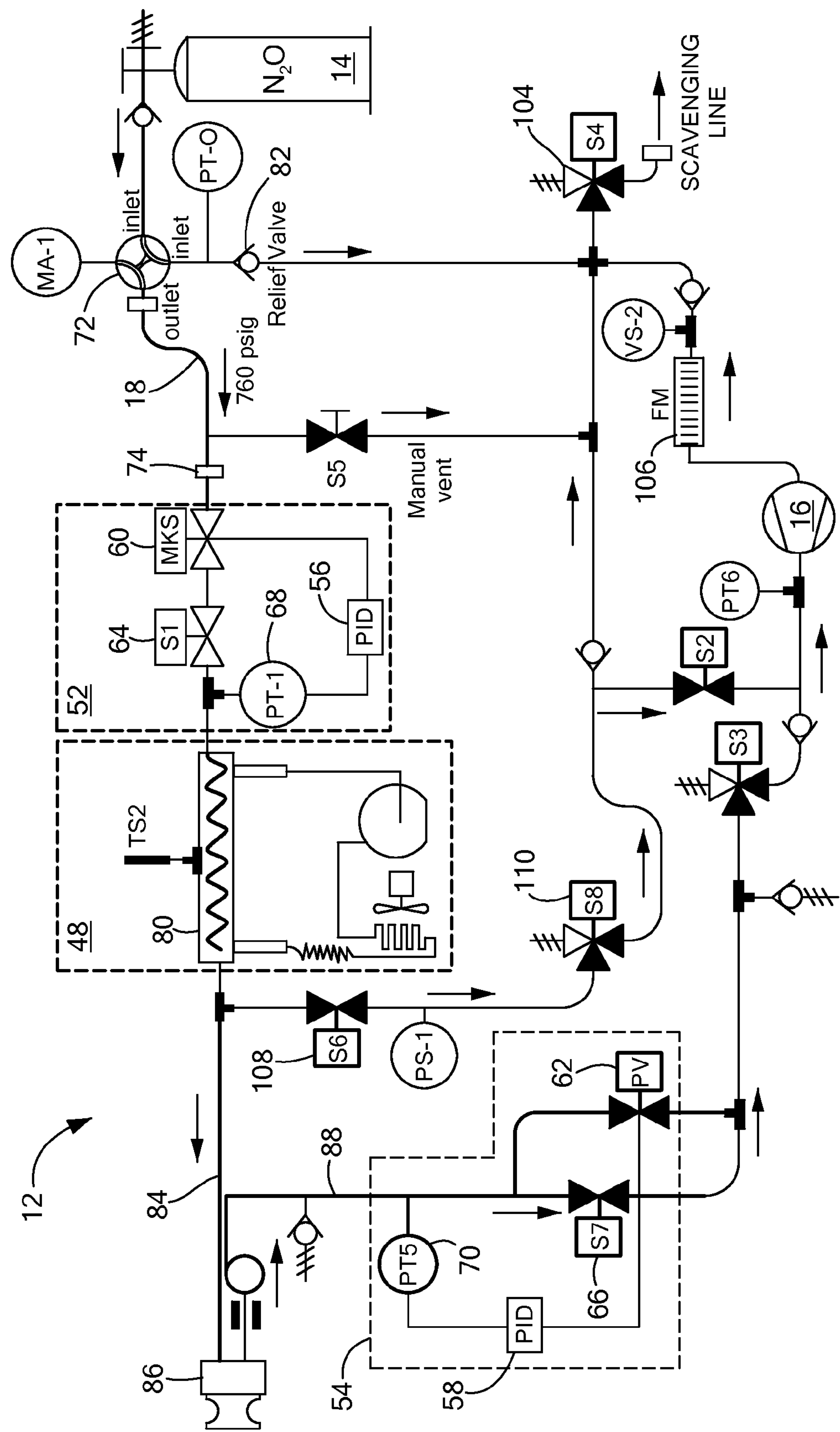
FIG. 2 shows a distal end of a cryotreatment device having an inflatable treatment element.

Referring now to FIG. 2, a first embodiment of a continuous flow cryotreatment system 12 is shown. The cryotreatment system 12 shown in FIG. 2 may be an improvement on an existing system, such as the Universal Gen V Cryoablation Console (Medtronic, Minneapolis, Minn.), which is a fixed initial volume system. The system 12 shown in FIG. 2 is a continuous flow system 12, and therefore may be used with any of a variety of cryotreatment devices. A cryotreatment device 10 with an inflatable or expandable treatment element 26, such as a cryoballoon, may be used with the systems 12 described herein (for example, as shown in FIG. 1). The system 12 of FIG. 2 may generally include a fluid supply reservoir 14, one or more pressure regulators, one or more pressure transducers, one or more valves for controlling the flow of fluid within the fluid flow path of the system 12, a subcooler system 48, an exhaust system that may include a vacuum pump 16 and fluid recovery reservoir 50, and one or more proportional-integral-derivative (PID) circuits 52, 54, each PID circuit 52, 54 including a PID controller 56, 58, a proportional valve 60, 62, a solenoid valve 64, 66, and a pressure transducer 68, 70. Additionally, the system 12 may include one or more controllers, processors, and/or software modules containing instructions or algorithms (collectively referred to as "computers 30") to provide for the automated operation and performance of the features, sequences, calculations, or procedures described herein. For example, a computer 30 may be in communication with one or more pressure transducers 68, 70 in the one or more PID circuits 52, 54 for the regulation of pressure and temperature based at least in part on pressure measurements communicated to the computer by the one or more pressure transducers 68, 70. That is, a feedback loop may be established between, at least, a PID circuit 52, 54 and the computer 30.

In the continuous flow system 12 shown in FIG. 2, an inflation reservoir is eliminated. Coolant (for example, $N_2O$) may be delivered from the fluid supply reservoir 14 through a pressure regulator 72, which may maintain the coolant pressure at approximately 750 psig to approximately 900 psig. The coolant may then pass through a stainless steel micron filter 74 that traps and removes system contaminants and/or particles larger than 0.5 micron. From the micron filter 74, the coolant may pass through an injection (or first) proportional valve 60 (MKS) and a first solenoid valve 64 (Si) of the first PID circuit 52. The coolant may then pass through the subcooler system 48, wherein the temperature of the coolant is reduced to ablation or treatment temperatures, and any gas bubbles are removed from the coolant to ensure that the coolant is in a liquid or substantially liquid state. The subcooler system 48 may include a heat exchanger 80 wherein heat is removed from the coolant, one or more compressors, one or more condensers, and/or other components for subcooling the coolant. The coolant may then pass through the fluid flow path 18 to the coaxial connector of the device 10 and eventually the expandable treatment element 26 of the device 10. A pressure relief valve 82, which may be set at approximately 1200 psig, may be installed in the fluid delivery line 86 to prevent over-pressurization of the system 12. The fluid delivery line 86 may be in communication with the injection lumen 40 disposed within the cryotreatment device 10 via a coaxial connector 86. Coolant may then pass through one or more lumens the elongate body 34 of the device 10 and exit the injection lumen 40 through the one or more holes or openings into the expansion chamber 38.

Upon exiting the injection lumen 40 into the expansion chamber 38, the pressurized coolant may rapidly expand. This expansion causes a reduction in temperature within the expansion chamber 38 and may cool the cryotreatment element 26 to a temperature at which the treatment element 26 may cool or ablate tissue. Expanded coolant may then pass into the exhaust lumen 42, which may be in communication with the return line 88 via the coaxial connector 86. Further, the exhaust lumen 42 and return line 88 may be in communication with an exhaust system, which may include a vacuum pump 16 and fluid recovery reservoir 50 or other scavenging elements (not shown). When in the return line 88, the expanded coolant may pass through one or more valves (for example, a solenoid valve 66 (S7) and return proportional valve 62 (PV)). Further, expanded coolant may travel through a three-way solenoid valve 104 (S4) before entering the fluid recovery reservoir 50 or similar scavenging elements. Coolant flow may be measured by a mass-flowmeter 106, located just downstream of the vacuum pump 16.

The system 12 may also include one or more valves for redirecting fluid and/or venting fluid to the atmosphere. For example, a solenoid valve 108 (S6) may be used to vent fluid from downstream of the subcooler system 48 (for example, to the fluid recovery reservoir 50 or other scavenging component). Further a three-way solenoid valve 110 (S8) may be used to vent to the atmosphere.

Continuing to refer to FIG. 2, the system 12 may include one or more pressure transducers 68, 70 that control the pressure of the injection line and/or the return line. For example, the system 12 shown in FIG. 2 includes a first pressure transducer 68 (PT1) upstream of the cryotreatment device 10 that is a component of a first PID circuit 52. The first PID controller 56 may drive first proportional valve 60 (MKS) that controls the injection pressure within the fluid delivery line 84. In general, this pressure may be considered to be a high pressure. For example, the pressure may be as high as between approximately 700 psi and approximately 760 psi. The first pressure transducer 68 (PT1) may communicate the internal pressure of the treatment element 26 (for example, a pressure within the expansion chamber 34) to a user, for example, by displaying a temperature value on a display 32 associated with the one or more computers 30. As a further example, the system 12 shown in FIG. 2 also includes a second pressure transducer 70 (PT5) downstream of the cryotreatment device 10 that is a component of a second PID circuit 54. The second PID controller 58 may drive second proportional valve 62 (PV) that controls the injection pressure within the return line 88. In general, this pressure may be considered to be a low pressure. Coolant may pass through a second solenoid valve 66 (S7) during the ablation phase or through the proportional valve (PV) during the continuous flow inflation phase.

During a cryoablation procedure, the two PID circuits 52, 54 may act simultaneously throughout the procedure to control both coolant injection and coolant return, depending on the desired treatment temperature. For example, the first PID circuit 52 may operate to decrease temperature of the coolant (for example, during the ablation phase of the procedure) by adjusting the first proportional valve 60 (MKS) to increase injection pressure and increase fluid flow. Further, the second PID circuit 54 may simultaneously operate to adjust the second proportional valve 62 (PV) to decrease pressure by opening the return line 88 (either partially or entirely) to the vacuum pressure generated by the vacuum pump 16, thereby increasing fluid flow. Conversely, the first PID circuit may operate to increase temperature of the coolant (for example, during the warming or thawing phase of the procedure) by adjusting the first proportional valve 60 (MKS) to decrease injection pressure and decrease fluid flow. Further, the second PID circuit 54 may simultaneously operate to adjust the second proportional valve 62 (PV) to increase pressure by closing the return line 88 (either partially or entirely) to the vacuum pressure generated by the vacuum pump 16, thereby decreasing fluid flow. In a warming phase following a cryoablation or cryotreatment phase, the treatment element 26 may reach temperatures well above cryoablation or cryotreatment temperatures, but that are sufficiently low to maintain cryoadhesion between the treatment element 26 and tissue. This is possible because the temperature of the coolant may be adjusted without ceasing coolant flow, as in fixed initial volume systems.

Increasing the coolant pressure will generally decrease coolant temperature, and vice versa. Additionally, the higher the flow rate of coolant through the treatment element 26, and the lower the temperature of that coolant, the more heat that may be removed from adjacent tissue. As coolant flow through the system 12 and through the treatment element 26 is increased, the temperature of the treatment element 26 is reduced, thus increasing the treatment element's capacity for cryoablation or cryotreatment of adjacent tissue. Unlike a fixed initial volume system in which a continuous flow is established only during the ablation phase, and in which the coolant is delivered to the treatment element at a constant temperature until coolant flow is stopped, the PID circuits 52, 54 in the system 12 of FIG. 2 allow for a continuous flow of coolant through the system 12 and through the treatment element 26 during the inflation phase, the cryoablation or cryotreatment phase, and a warming or thawing phase. For example, the treatment element 26 may be allowed to reach thawing temperatures, and therefore break cryoadhesion, at the end of a procedure in order to remove the cryotherapeutic device 10 from the treatment site. Conversely, the treatment element 26 may be maintained at temperatures above those at which cryoadhesion is broken if a warming phase will be followed by an ablation phase.

Figure 3:
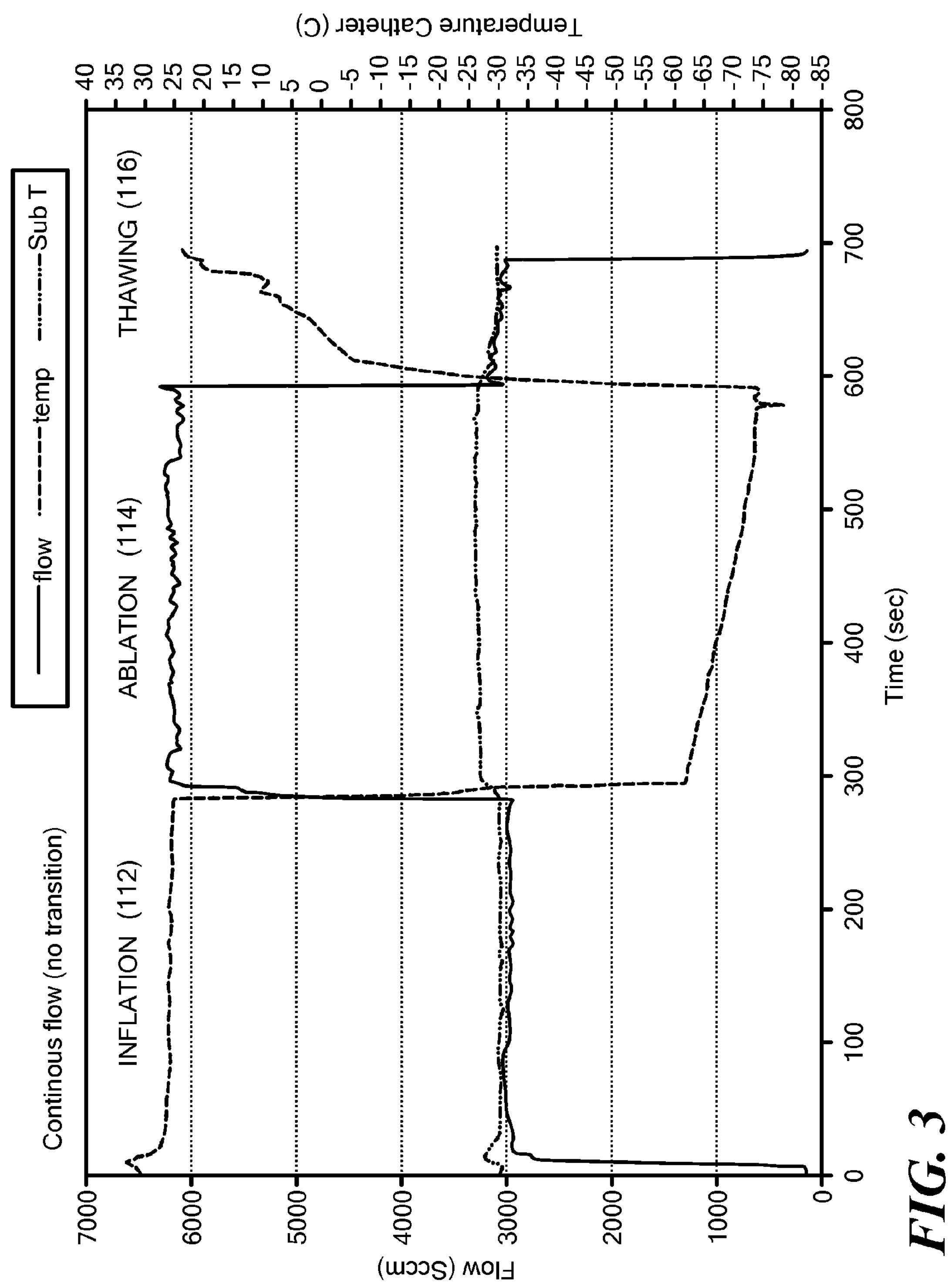
FIG. 3 shows a graphical representation of system temperatures and coolant flow as is achieved by a continuous flow cryotreatment system in accordance with the present invention.

Referring now to FIG. 3, a graphical representation of system 12 temperatures (line "temp") and coolant flow (line "flow") as is achieved by a continuous flow cryotreatment system 12 in accordance with the present invention is shown. As shown in FIG. 3, fluid flow may increase from zero to between approximately 2500 standard cubic centimeters per minute (sccm) and approximately 3500 sccm during the inflation phase 112. Consequently, temperature within the expansion chamber 34 may be between approximately 20° C. and approximately 40° C. Unlike a fixed initial volume system, the continuous flow systems 12 described herein do not require a transition phase. During the cryoablation or cryotreatment phase 114, the flow rate may increase to between approximately 6000 sccm and approximately 7000 sccm. Consequently, temperature within the expansion chamber 34 may be between approximately −55° C. and approximately −80° C. During a warming or thawing phase 116, fluid flow may decrease to approximately 3200 sccm or below, depending on whether warming or complete thawing is desired. FIG. 3 also shows a line representing the fluid flow and temperature of coolant within the subcooler system (line "Sub T"), both of which remain relatively constant through all phases of the procedure.

Figure 4:
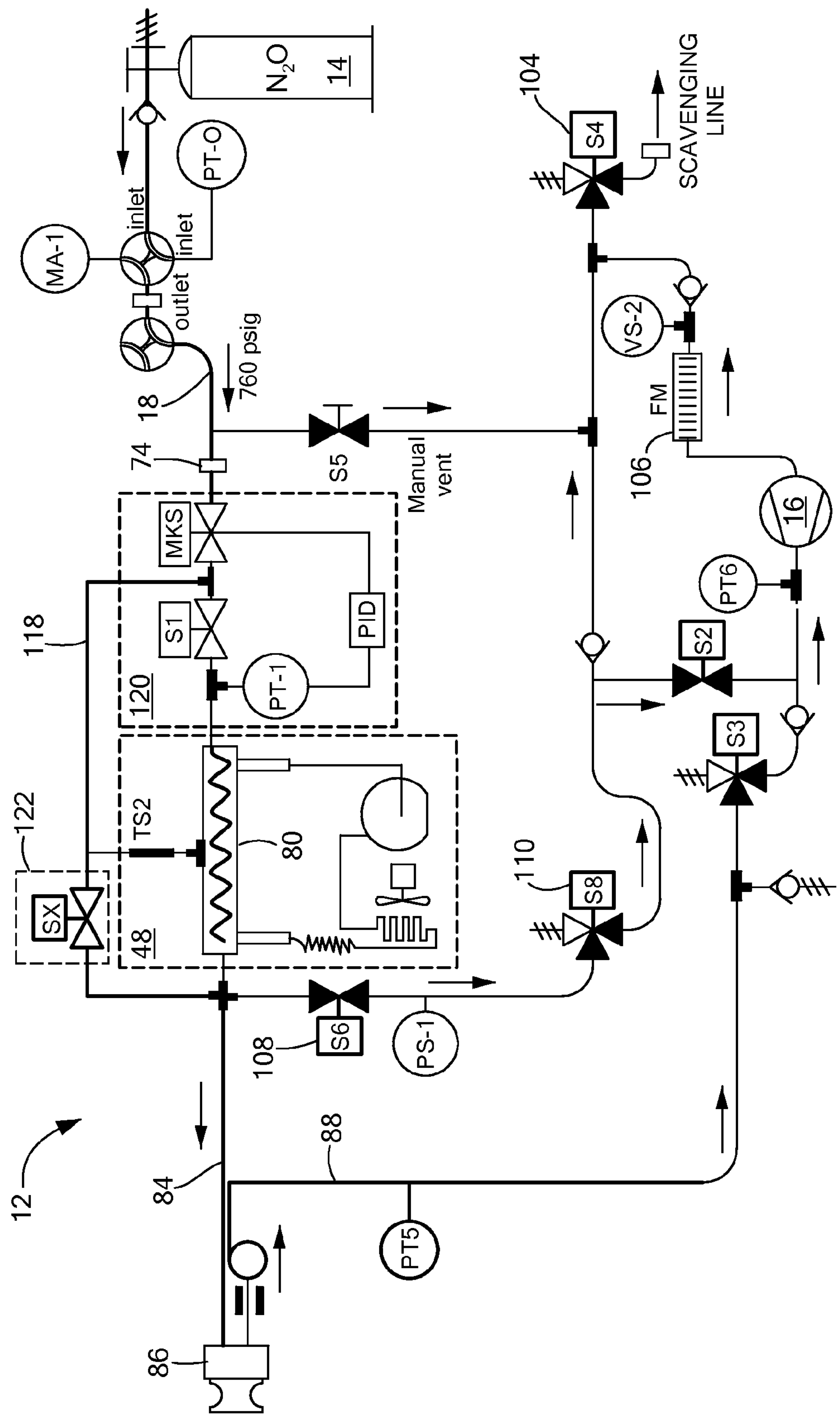
FIG. 4 shows a schematic view of a second embodiment of a continuous flow cryotreatment system in accordance with the present invention.

Referring now to FIG. 4, a second embodiment of a continuous flow cryotreatment system 12 is shown. The system 12 of FIG. 4 may generally be similar to the system 12 of FIG. 2; however, in the system 12 of FIG. 4, the temperature of the treatment element 26 may be adjusted not by the use of one or more PID circuits, but by including a fluid flow path 118 that bypasses the subcooler 48. The cryotreatment system 12 shown in FIG. 4 may be an improvement on an existing system, such as the Universal Gen IV Cryoablation Console, which is a fixed initial volume system that does not include a proportional valve on the return line.

As in shown in FIG. 4, a bypass fluid line 118 may be added that extends from the PID circuit 120 to downstream of the subcooler system 48. Further, the bypass fluid line 118 may include a two-way solenoid valve 122 (SX) that may be opened or substantially opened to allow coolant to bypass the subcooler system 48 and closed or substantially closed to allow coolant to enter the subcooler system 48. For example, the solenoid valve 122 (SX) may be open to bypass the subcooler system 48 during the inflation phase when it is undesirable to use coolant that is cooled to cryoablation or cryotreatment temperatures. Further, the solenoid valve 122 (SX) may be closed during the ablation phase, which allows coolant to flow through the subcooler system 48 in order to reach cryoablation or cryotreatment temperatures.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A continuous flow cryotreatment system, the cryotreatment system comprising:

a fluid supply;

a fluid injection line in communication with the fluid supply, the fluid injection line including a first PID circuit having a first PID controller, a first pressure transducer, and a first proportional valve;

a cryotreatment device having a treatment element in communication with the fluid injection line;

a fluid return line in communication with the cryotreatment device, the fluid return line including a second PID circuit having a second PID controller, a second pressure transducer, and a second proportional valve;

a vacuum source in communication with the fluid return line; and the system being programmed to operate in an inflation phase, a treatment phase, and a warming phase, the first PID circuit and second PID circuit simultaneously operating to control the temperature of the treatment element during the inflation phase, the ablation phase, and the warming phase, the system being further programmed such that simultaneous operation of the first PID circuit and the second PID circuit being configured to continuously deliver a cryotreatment fluid to the cryotreatment device during all of the inflation phase, ablation phase, and warming phase.

2. The system of claim 1, wherein the treatment element defines an expansion chamber, the expansion chamber being in communication with the fluid injection line and the fluid return line, the treatment element having an adjustable temperature based at least in part on the flow of fluid within the expansion chamber from the fluid supply reservoir.

3. The system of claim 2, wherein the system further comprises a control unit in communication with the first PID circuit and the second PID circuit, first pressure transducer and the second pressure transducer each measuring pressure within the system, the control unit adjusting the first proportional valve and the second proportional valve based at least in part on the pressure measurements of the first proportional valve and the second proportional valve.

4. The system of claim 3, wherein the first pressure transducer measures pressure within the expansion chamber of the cryotreatment device.

5. The system of claim 3, wherein the temperature of the treatment element is decreased when the first proportional valve is adjusted to increase the flow rate of coolant into the expansion chamber and when the second proportional valve is adjusted to at least partially open the expansion chamber to the vacuum source.

6. The system of claim 5, wherein the temperature of the treatment element is increased when the first proportional valve is adjusted to reduce the flow rate of coolant into the expansion chamber and when the second proportional valve is adjusted to at least partially close the expansion chamber to the vacuum source.

7. The system of claim 6, wherein the treatment element is an inflatable element, the inflatable element remaining inflated throughout the treatment phase and warming phase.

8. The system of claim 7, wherein the treatment element is positioned proximate an area of target tissue during the treatment phase and the warming phase.

9. The system of claim 8, wherein the temperature of the treatment element during the warming phase is less than approximately 0° C. but greater than a temperature at which the treatment element ablates the target tissue.

10. The system of claim 9, wherein the first PID circuit and the second PID circuit each further include a solenoid valve.

11. The system of claim 1, wherein the first PID circuit controls a fluid injection pressure within the fluid injection line.

12. The system of claim 1, wherein the second PID circuit controls a fluid injection pressure within the fluid return line.

* * * * *